(12) United States Patent
Pekonen et al.

(10) Patent No.: US 10,602,937 B2
(45) Date of Patent: Mar. 31, 2020

(54) PHOTOPLETHYSMOGRAPHIC SENSOR CONFIGURATION

(71) Applicant: Polar Electro Oy, Kempele (FI)

(72) Inventors: Elias Pekonen, Oulu (FI); Seppo Korkala, Kempele (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 15/637,447

(22) Filed: Jun. 29, 2017

(65) Prior Publication Data

US 2018/0000363 A1  Jan. 4, 2018

(30) Foreign Application Priority Data

Jul. 1, 2016 (GB) .................................. 1611542.0

(51) Int. Cl.
*A61B 5/024* (2006.01)
*A61B 5/00* (2006.01)
(Continued)

(52) U.S. Cl.
CPC ........ *A61B 5/02427* (2013.01); *A61B 5/0205* (2013.01); *A61B 5/0255* (2013.01);
(Continued)

(58) Field of Classification Search
None
See application file for complete search history.

(56) References Cited

U.S. PATENT DOCUMENTS

2014/0275854 A1* 9/2014 Venkatraman ..... A61B 5/02416
600/301
2015/0230743 A1* 8/2015 Silveira .............. A61B 5/14552
600/323

(Continued)

FOREIGN PATENT DOCUMENTS

CN  104173035 A  12/2014
KR  20120057813 A  6/2012
(Continued)

OTHER PUBLICATIONS

Examination Report, Application No. GB1611542.0, 4 pages, dated Jan. 13, 2017.
(Continued)

*Primary Examiner* — Bill Thomson
*Assistant Examiner* — Shahdeep Mohammed
(74) *Attorney, Agent, or Firm* — FisherBroyles, LLP (57) ABSTRACT

An apparatus is suitable for measuring a photoplethysmogram (PPG). A photoplethysmographic sensor apparatus may include a casing defining a surface, a plurality of optical emitters configured to emit radiation extending from the surface, at least one photo sensor configured to capture radiation emitted by at least a subset of the plurality of optical emitters. At least a first measurement configuration and a second configuration is defined by the plurality of optical emitters and the at least one photo sensor such that the first and the second measurement configuration provide different measurement channels by including at least partially different sets of at least one optical emitter and at least one photo sensor. The first and second measurement configurations define different spatial configurations, each of which is line symmetric with respect to an imaginary line along the surface.

13 Claims, 9 Drawing Sheets

(51) Int. Cl.
*A61B 5/1455* (2006.01)
*A61B 5/0205* (2006.01)
*A61B 5/0255* (2006.01)
*A61B 5/11* (2006.01)

(52) U.S. Cl.
CPC ...... *A61B 5/02405* (2013.01); *A61B 5/02416* (2013.01); *A61B 5/02438* (2013.01); *A61B 5/1123* (2013.01); *A61B 5/1455* (2013.01); *A61B 5/14552* (2013.01); *A61B 5/4809* (2013.01); *A61B 5/681* (2013.01); *A61B 5/6843* (2013.01); *A61B 5/721* (2013.01); *A61B 5/7214* (2013.01); *A61B 5/7475* (2013.01); *A61B 5/6801* (2013.01); *A61B 5/6816* (2013.01); *A61B 5/6817* (2013.01); *A61B 5/6824* (2013.01); *A61B 5/6844* (2013.01); *A61B 5/7257* (2013.01); *A61B 5/74* (2013.01); *A61B 2503/10* (2013.01); *A61B 2560/0412* (2013.01); *A61B 2560/0462* (2013.01); *A61B 2562/0233* (2013.01); *A61B 2562/0238* (2013.01); *A61B 2562/04* (2013.01); *A61B 2562/043* (2013.01); *A61B 2562/046* (2013.01)

(56) References Cited

U.S. PATENT DOCUMENTS

| | | | |
|---|---|---|---|
| 2015/0366469 A1 | 12/2015 | Harris et al. | |
| 2016/0058312 A1* | 3/2016 | Han | G01N 21/55 600/473 |
| 2016/0367154 A1* | 12/2016 | Gladshtein | F16L 33/30 |
| 2017/0007138 A1* | 1/2017 | Kim | A61B 5/02427 |
| 2018/0192965 A1* | 7/2018 | Rose | A61B 5/743 |

FOREIGN PATENT DOCUMENTS

| | | |
|---|---|---|
| WO | 2015084375 A1 | 6/2015 |
| WO | 2016096409 A1 | 6/2016 |

OTHER PUBLICATIONS

Combined Search and Examination Report, Application No. GB1611542.0, 9 pages, dated Aug. 31, 2016.
Examination Report, Application No. GB1611542.0, 2 pages, dated Apr. 21, 2017.
Response Made to Report, Application No. GB1611542.0, 1 page, dated Jun. 27, 2017.

* cited by examiner

PHOTOPLETHYSMOGRAPHIC SENSOR CONFIGURATION

CROSS-REFERENCE TO RELATED APPLICATION

This application claims benefit to United Kingdom Application No. 1611542.0, filed Jul. 1, 2016, which is incorporated by reference herein in its entirety.

BACKGROUND

Field

The invention relates to photoplethysmographic sensors configured to optically measure heart activity of a user.

Description of the Related Art

A conventional sensor configuration configured to measure photoplethysmogram comprises two emitter heads configured to radiate energy with optical wavelength and a photodiode or a similar optical sensor disposed between the emitter heads. Radiation emitted by the emitters reflect from a human tissue, e.g. in an arm or ear of a user, and some features of the reflected radiation are a function of the user's heart activity. A blood pulse wave travelling in arteries modulates the reflected radiation which enables measurement of the heart activity by analyzing a signal captured by the optical sensor.

SUMMARY

The invention is defined by the subject-matter of the independent claims. Embodiments are defined in the dependent claims.

BRIEF DESCRIPTION OF DRAWINGS

In the following, the invention will be described in greater detail with reference to the embodiments and the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
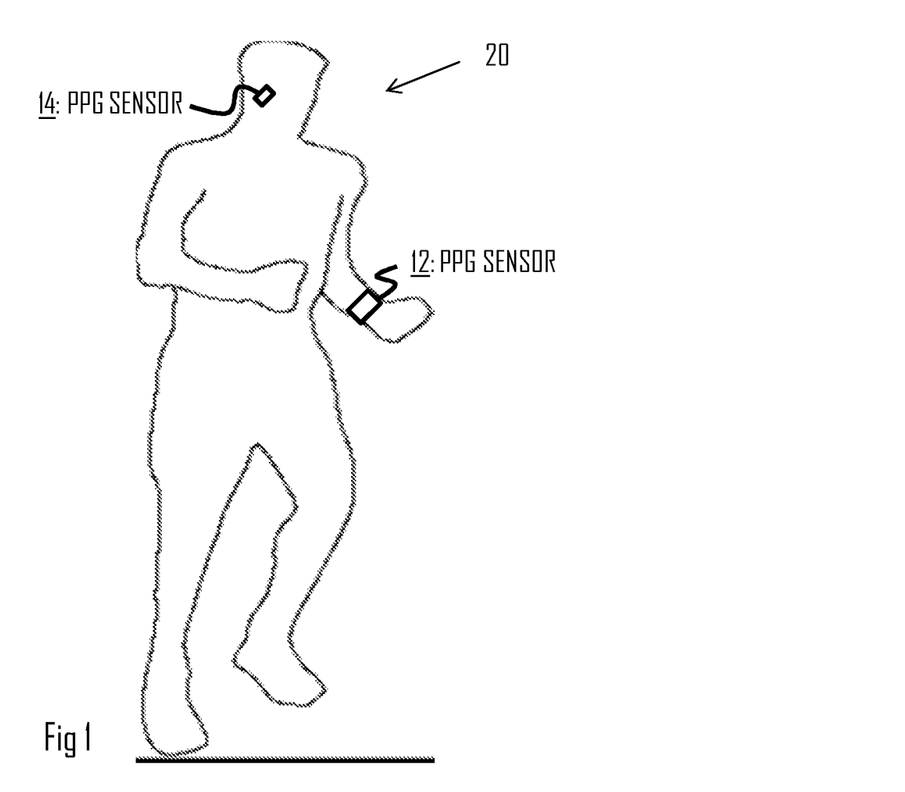
FIG. 1 illustrates a general measurement scenario to which embodiment of the invention may be applied.

FIG. 1 illustrates a measurement system comprising sensor devices that may be used in the context of some embodiments of the present invention. The sensor devices 12, 14 may be configured to measure a photoplethysmogram (PPG) optically. PPG represents a volumetric measurement of an organ. A PPG sensor 12, 14 may comprise an emitter configured to emit radiation. The emitter may be a light emitting diode (LED) configured to illuminate a skin of a user 20. The PPG sensor may further comprise a light-sensitive photo sensor such as a photodiode configured to measure changes in light reflected from the illuminated skin. With each cardiac cycle, the heart pumps blood to peripheral arteries. Even though this blood wave pulse is damped by the artery system as it propagates, it is enough to distend arteries and arterioles in the subcutaneous tissue. If the emitter and the photo sensor are placed appropriately against the skin, the blood wave pulse can be detected as a change in the reflecting light measured by using the photo sensor. Each cardiac cycle appears as a change in a measurement signal acquired through the photo sensor. A typical application is optical measurement of user's 20 heart activity such as heart rate. The blood pulse wave may be modulated by multiple other physiological systems and, therefore, the PPG may also be used to monitor breathing, oxygen saturation, and other physiological conditions, even medical symptoms, disorders, and diseases. The PPG may be measured at various locations of the human body, e.g. from a wrist (sensor 12), head, ear canal or ear leaf (sensor 14).

Figure 2:
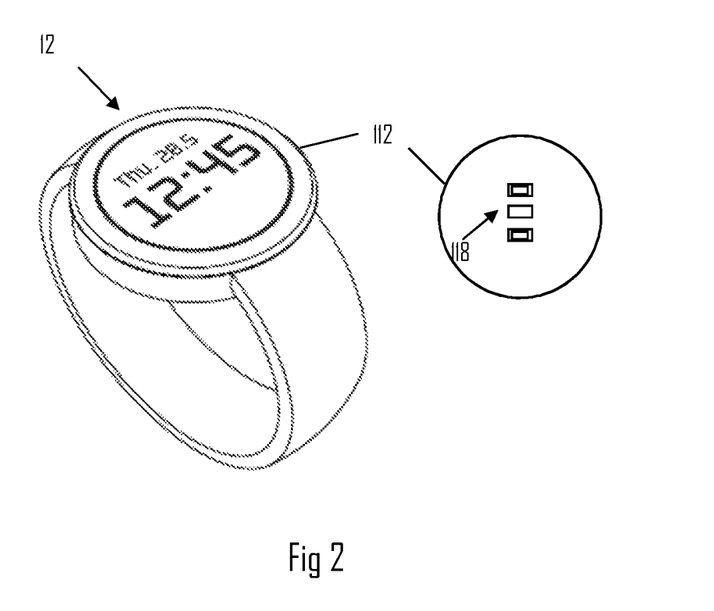
FIG. 2 illustrates an apparatus to which embodiments of the invention may be applied.

FIG. 2 illustrates a PPG sensor device 12 in the form of a wrist device. The wrist device 12 may be a training computer configured to measure heart activity of the user 20 during a physical exercise. Additionally, the wrist device may be configured to measure daily activity of the user 20 continuously or at least whenever the wrist device 12 is attached to the user 20. At least some PPG sensor configurations may be associated with both of these measurement schemes. The PPG sensor may be provided on a backside of a casing of the wrist device 12, wherein the backside is arranged to face the user's skin. The backside of the casing facing the user's skin may define a surface 112 that is substantially aligned with the user's skin in the attachment location. A PPG sensor configuration 118 may be provided such that one or more emitters of the PPF sensor configuration 118 emit radiation extending from the surface to the user's skin and, further, that at least one photo sensor is aligned to receive the emitted radiation as reflected from the user's skin.

According to an embodiment of the invention, there is provided a PPG sensor apparatus comprising: a casing defining a surface 112, a plurality of optical emitters configured to emit radiation extending from the surface 112, and at least one photo sensor configured to capture radiation emitted by at least a subset of the plurality of optical emitters. At least a first measurement configuration and a second configuration is defined by the plurality of optical emitters and the at least one photo sensor such that the first and the second measurement configuration provide different measurement channels by comprising at least partially different sets of at least one optical emitter and at least one photo sensor. Furthermore, the first and second measurement configurations define different spatial configurations each of which is line symmetric with respect to an imaginary line along the surface. Symmetricity with respect to the line may be understood such that the element(s) of the measurement configuration on one side of the line form a mirror image of the element(s) of the measurement configuration on the opposite side of the line. In an embodiment, multiple measurement configurations or even every measurement configuration provided in the apparatus comprise multiple elements on both sides of the line of symmetry. In an embodiment, multiple measurement configurations or even every measurement configuration provided in the apparatus includes at least one element (an emitter and/or a photo sensor) that is completely on one side of the line of symmetry.

Figure 3:
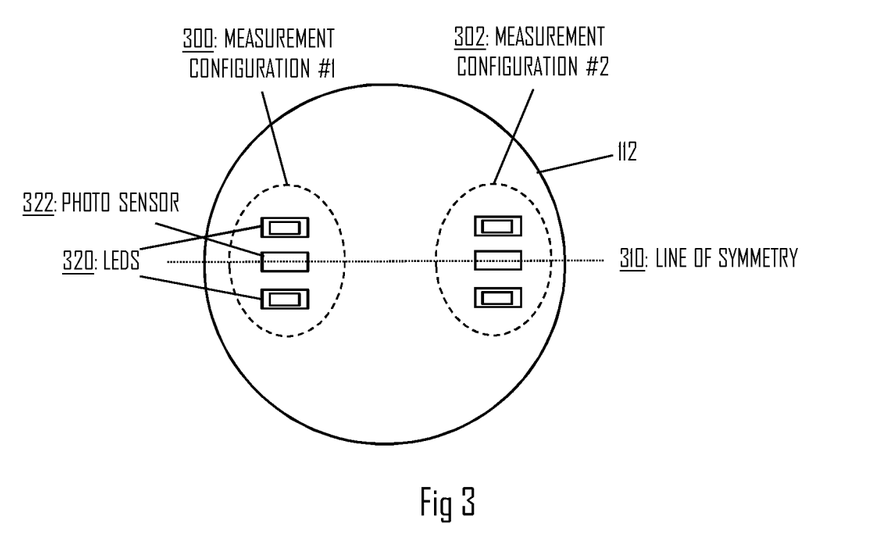
FIGS. 3 to 6 illustrate sensor head arrangements for a photoplethysmographic (PPG) sensor according to some embodiments of the invention.

FIGS. 3 to 6 illustrate different spatial arrangements of PPG sensor heads. In the Figures, an optical emitter is illustrates with a rectangle arrangement consisting of an inner rectangle inside an outer rectangle. A photo sensor is illustrated by a single rectangle. A sensor head may be comprised of a set of optical emitters and one or more photo sensors. FIG. 3 illustrates an embodiment comprising two distinct PPG sensor heads, each sensor head comprising a photo sensor 322 and two emitters (LEDs) 320. A first sensor head forming a first measurement configuration 300 comprises a first photo sensor 322 and two emitters 320 disposed on opposite sides of the photo sensor 322. A second sensor head forming a second measurement configuration 302 comprises a second photo sensor, different from the first photo sensor 322, and two emitters disposed on opposite sides of the second photo sensor. The two sensor heads may be disposed remotely with respect to one another on the surface 112, e.g. on opposite edges of the surface. Remote in this context may be defined such that radiation emitted from the emitters of one measurement configuration cannot reach a photo sensor of the other measurement configuration when the device is in use and attached to the user's skin. Or even if a low degree of light reaches the photo sensor of the different measurement configuration, the level is so low that it does not degrade the measurement accuracy notably. Accordingly, the first and second measurement configurations 300, 302 are spatially so distant that they provide mutually orthogonal measurement channels. FIG. 3 illustrates the line of symmetry 310 along which the measurement configurations are disposed in a line-symmetric manner. The line of symmetry travels via the photo sensors on the surface such that emitters of the measurement configuration are disposed line-symmetrically about the line of symmetry 310. In other words, the emitters 320 are provided at equal distances from the photo sensor 322. Such a configuration provides an advantage when the measurements are carried out while the user 20 is moving, e.g. running or swimming. If the apparatus moves with respect to the user's skin, one of the emitters 320 of a measurement configuration may be detached from the skin contact. Then, less light may reach from this emitter to the photo sensor 322. With suitable spatial arrangement of the sensor head, the motion may force the other emitter to press more firmly against the skin, thus providing a better skin contact and increased amount of light reaching the photo sensor 322. Accordingly, the symmetric arrangement may provide compensation against motion artefacts in measurement signals measured with the photo sensor 322. In the embodiment of FIG. 3, the two measurement configurations may be spatially arranged such that the line of symmetry 310 is perpendicular to a longitudinal axis of a strap attaching the apparatus to the user's wrist (or arm). Accordingly, the line of symmetry 310 also defines a rotational axis for the movement of the apparatus with respect to the user's skin. This means that the surface rotates slightly about the rotational axis when the apparatus moves during the motion of the user's hand, which creates the above-described function of the emitters 320 moving to opposite directions with respect to the user's skin. In another embodiment, the sensor heads of the different measurement configurations 300, 302 are arranged spatially such that the line of symmetry 310 is aligned, i.e. is parallel with the longitudinal axis of the strap. The functional use of the measurement configurations 300, 302 is described below.

Figure 4:
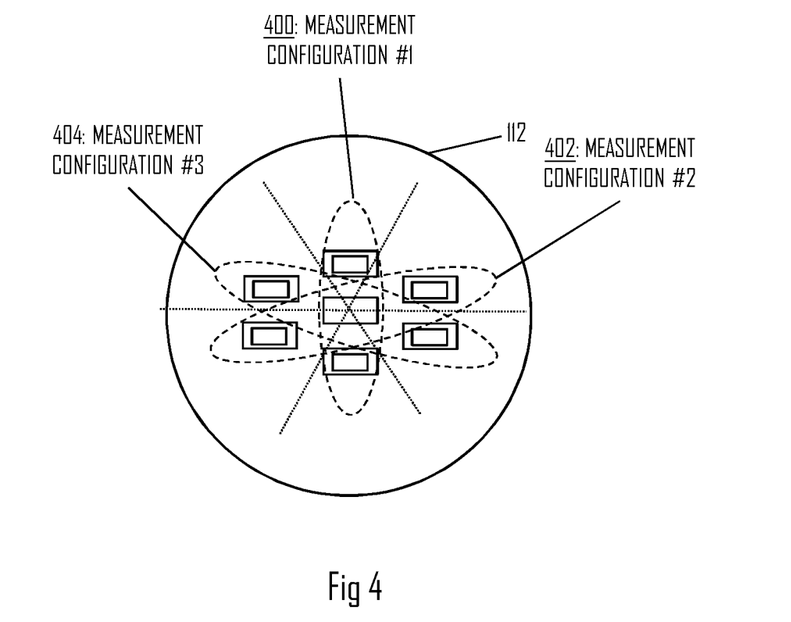

In the embodiment of FIG. 3, the measurement configurations 300, 302 are both line-symmetric with respect to the same line of symmetry 310. FIG. 4 illustrates a PPG sensor configuration where different measurement configurations 400, 402, 404 are line-symmetric with different imaginary symmetric lines on the surface 112. In this embodiment, the different measurement configurations 400 to 404 employ the same photo sensor and each have distinct emitters, wherein the emitters are disposed around the photo sensor. In this arrangement, the emitters are all disposed at the same distance from the photo sensors and spatially arranged on an imaginary annulus formed on the surface. The emitters may also be disposed uniformly on the annulus. A measurement configuration consists of the photo sensor and two emitters disposed on opposite sides with respect to the photo sensor. This arrangement may provide for even better compensation against the motion artefacts. In many occasions, the motion is back-and-forth motion in a certain direction, thus degrading the performance of one of the measurement configurations 400, 402, 404 while another measurement configuration is not affected by the motion. Accordingly, providing multiple measurement configurations disposed symmetrically about differently aligned lines of symmetry may provide better performance under the influence of motion.

In some embodiments where the different measurement configurations are line-symmetric with respect to different lines of symmetry, the lines of symmetry are parallel, i.e. aligned with respect to each other but are at different locations on the surface. In other embodiments where the different measurement configurations are line-symmetric with respect to different lines of symmetry, the lines of symmetry are rotated with respect to each other on the surface. FIG. 4 illustrates such an embodiment. The lines of symmetry may be rotated in a regular manner such that an angle of rotation between consecutive rotations is a constant, e.g. 60 degrees in the embodiment of FIG. 4.

Figure 5:
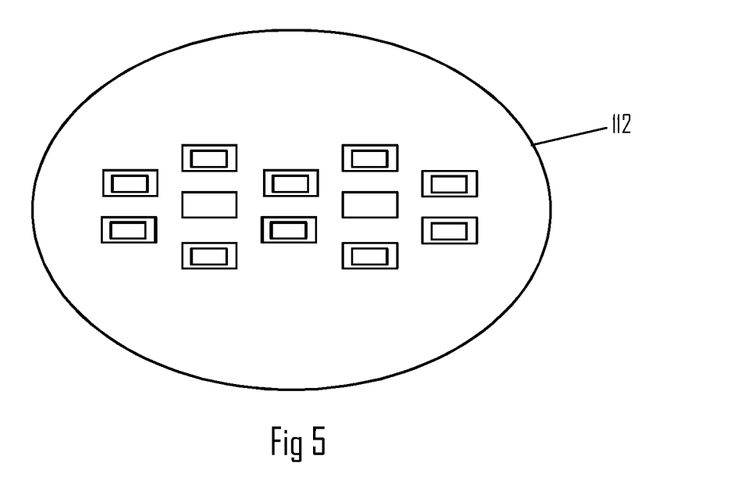

FIG. 5 illustrates a modification of the embodiment of FIG. 4, wherein two photo sensors are provided and emitters disposed symmetrically around each photo sensor. The measurement configurations may be arranged in a manner similar to the embodiment of FIG. 4 where emitters disposed symmetrically on opposite sides of a photo sensor form a measurement configuration. Some emitters provided between the photo sensors may belong to multiple measurement configurations. This analogy may be expanded to large sensor arrays with numerous photo sensors and optical emitters. In an embodiment, the photo sensors and/or the emitters form a matrix where measurement configurations are formed from the elements of the matrix such that each measurement configuration comprises at least one emitter and at least one photo sensor of the matrix. The matrix may comprise multiple rows and multiple columns formed by the photo sensors and the emitters. In an embodiment, the size of the matrix may be 10×5, 5×10, 10×10, or even higher. Some elements of the matrix may be photo sensors while other elements are optical emitters. Such an arrangement may enable arbitrary selection of the measurement configurations which enables very flexible adaptation to various measurement conditions. The measurement configurations need not to be fixed but a controller controlling the apparatus may select and adjust the components of the measurement configurations during in operation.

In the embodiments of FIGS. 3 to 5, the number of emitters has been higher than the number of photo sensors. It is a typical arrangement because emitters such as LEDs are cheaper to manufacture than the photo sensors, e.g. photo diodes. However, the locations of the emitters and the photo sensors may be switched such that photo sensors may be provided at the locations of the emitters and emitters provided in locations of the photo sensor(s) in FIGS. 3 to 5.

In the embodiments of FIGS. 3 to 5, each measurement configuration may provide for a single measurement channel. Basically, each measurement configuration provides two different emitter-sensor pairs and, thus, at least two distinct light paths. However, when the emitters of the measurement configuration radiated concurrently, the photo sensor combines the light paths into a single logical measurement channel.

Figure 6:
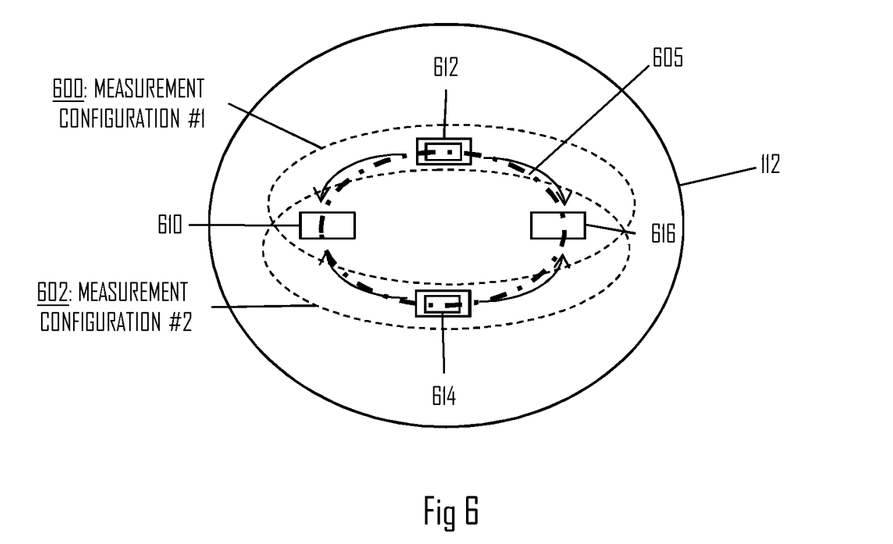

FIG. 6 illustrates yet another PPG sensor head configuration suitable for the wrist device 12 or the ear device 14. The embodiment of FIG. 6 comprises a plurality of photo sensors 610, 616 arranged along an imaginary annulus 605 (illustrated by dash-dotted line in FIG. 6) on the surface 112 in an alternating manner with a plurality of optical emitters 612, 614. In the embodiment of FIG. 6, two photo sensors 610, 616 are provided on opposite sides of the annulus, and two emitters 612, 614 are provided on opposite sides of the annulus. A first measurement configuration 600 consists of a first optical emitter and photo sensors 610, 616 adjacent with respect to the first optical emitter along the annulus 605, and a second measurement configuration 602 consists of a second optical emitter 614 and photo sensors 610, 616 adjacent with respect to the second optical 614 emitter along the annulus 605. Both measurement configurations 600, 602 use the same photo sensors 610, 616 but different emitters 612, 614.

Arrows from the emitters to the photo sensors illustrate measurement channels. As can be seen, the arrangement provides four distinct measurements channels, two per measurement configuration 600, 602. That is, radiation emitted by the emitter 612 is received in the photo sensors 610, 616 via distinct paths, and radiation emitted by the emitter 614 is received in the photo sensors 610, 616 via distinct paths. This applies to reflections from an ear lobe, reflections from an ear canal, and reflections from a wrist or arm.

Figure 7:
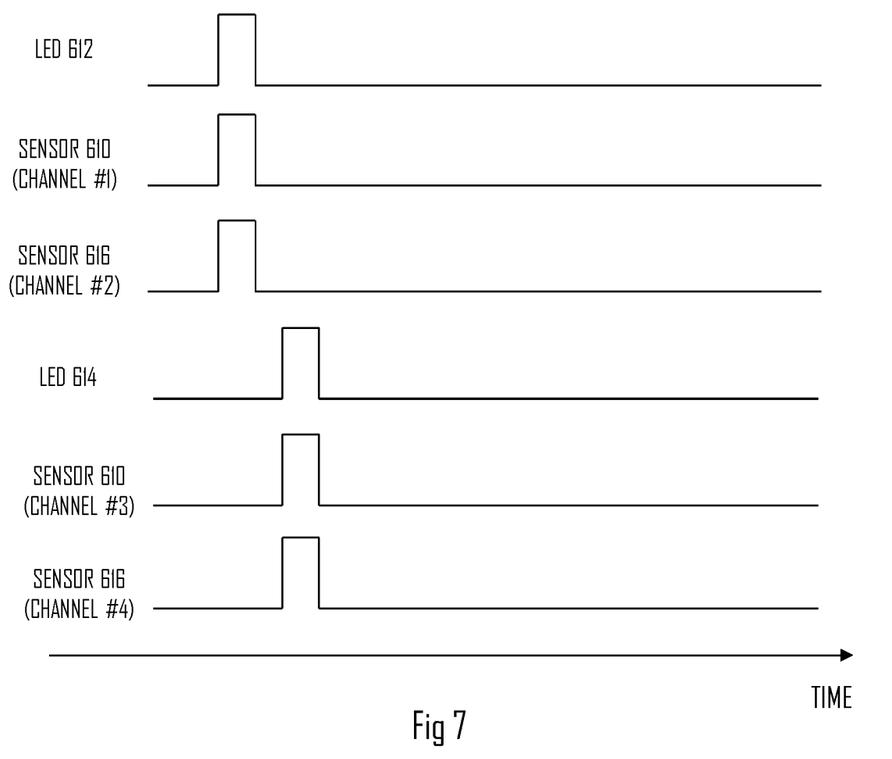
FIGS. 7 to 9 illustrate solutions for time-multiplexing operation of multiple PPG measurement configurations according to some embodiments of the invention.

In an embodiment, the operation of the multiple measurement configurations is multiplexed to provide mutually orthogonal measurement configurations. In an embodiment, the emitters of the measurement configurations are configured to emit radiation in a time-multiplexed manner. FIG. 7 illustrates an embodiment for controlling the emission timing in the embodiment of FIG. 6. As seen in FIG. 7, the emitter (LED) 612 emits at different time than the emitter 614 and the emitters 612, 614 do not emit at the same time.

The emitters 612 614 may be configured to emit in a periodic manner with different timing offsets to realize the time-multiplexing. The duty cycle of the emission periodicity may be low in the sense that "on" duration of an emitter may be significantly lower than "off" duration. The duty cycle may be lower than ⅒, lower than 1/100, lower than 0.5/100 or even lower. This provides flexibility to the time-multiplexing when the number of measurement configurations is high, e.g. the matrix configuration described above. In such configurations, the number of operational measurement configurations and the number of available measurement channels may be very high, e.g. ten or over, 100 or over.

When the emitter 612 is emitting light, the photo sensors 610, 616 associated with the respective measurement channels #1 and #2 receive the radiation and generate respective measurement signals dependent on the received radiation. Similarly, when the emitter 614 is emitting light, the photo sensors 610, 616 associated with the respective measurement channels #3 and #4 receive the radiation and generate respective measurement signals dependent on the received radiation. Accordingly, a processor processing the measurement data acquires four distinct measurement signals associated with the different measurement channels. The processor may then use this diversity to improve accuracy of heart activity measurements, e.g. by combining the measurement signals in an attempt to reduce motion artefacts as described in greater detail below.

Figure 8:
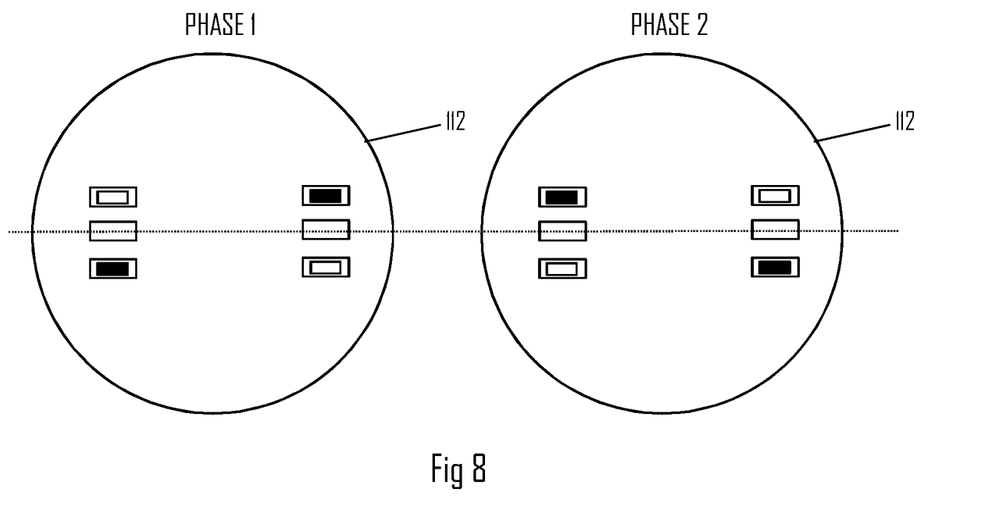

FIG. 8 illustrates the time-multiplexing in the embodiment of FIG. 3. The line of symmetry is again illustrated in FIG. 8 to facilitate the reader. In this embodiment, the emitters of each measurement configuration 300, 302 are switched on sequentially. Furthermore with respect to the operation of the different measurement configurations, emitters on opposite sides of the line of symmetry in the different measurement configurations are illuminated simultaneously. In other words, those emitters that are spatially the most distant with respect to each other are illuminated simultaneously. As illustrated in FIG. 1, in a first phase the following emitters are configured to radiate: 1) an emitter of the first measurement configuration on a first side of the line of symmetry and 2) an emitter of the second measurement configuration on a second, opposite side of the line of symmetry. Further, in a second phase the following emitters are configured to radiate: 1) an emitter of the first measurement configuration on the second side of the line of symmetry and 2) an emitter of the second measurement configuration on the first side of the line of symmetry. Such a configuration minimizes the interference between the different measurement configurations. However, it should be appreciated that the duty cycles described above enable illumination of a total of one emitter at a time.

In another embodiment, emitters on the same side of the line of symmetry in the different measurement configurations are illuminated simultaneously. When the distance between the sensor heads of the different measurement configurations is sufficiently high, this configuration may result in corresponding performance as the sequence illustrated in FIG. 8.

Figure 9:
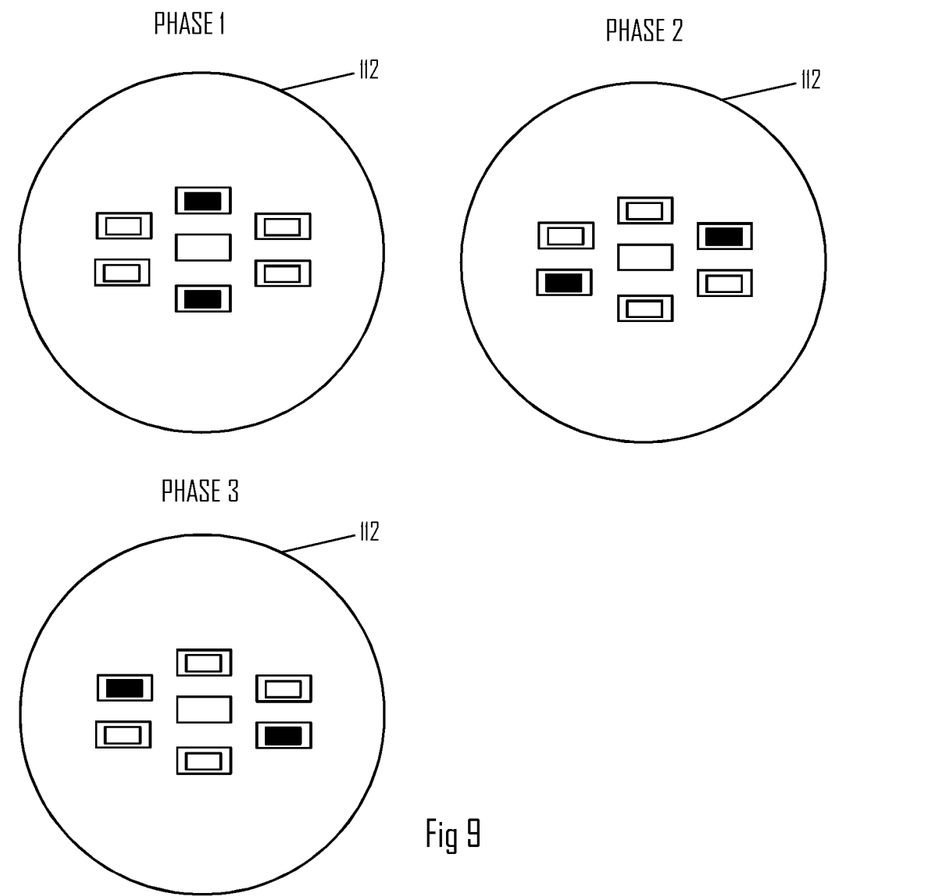

FIG. 9 illustrates the time-multiplexing in the embodiment of FIG. 4. In this embodiment, all the emitters of a measurement configuration emit at the same time, and the time-multiplexing is arranged only between the different measurement configurations. In the first phase, only the emitters of the first measurement configuration 400 are configured to emit radiation. Subsequently, only the emitters of the second measurement configuration 402 are configured to emit radiation in the second phase. Subsequently, only the emitters of the third measurement configuration 404 are configured to emit radiation in the third phase. In this manner, only the emitters on the opposite sides of the photo sensor emit radiation concurrently.

Figure 10:
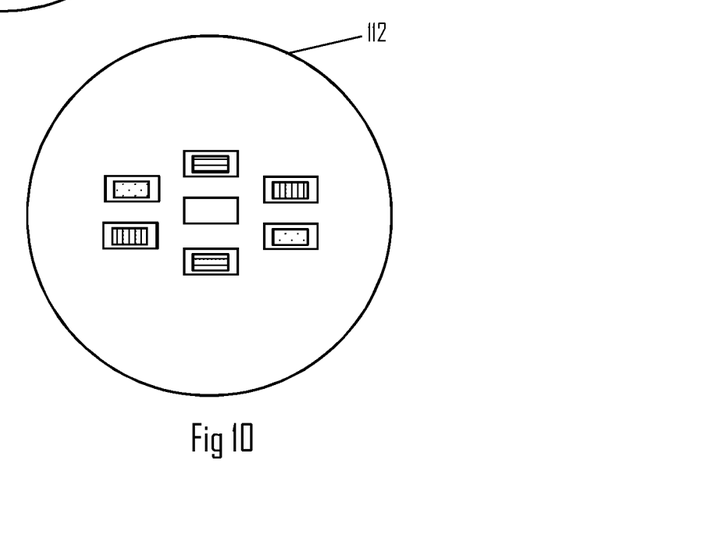
FIG. 10 illustrates an embodiment for carrying out the multiplexing in a different manner.

FIG. 10 illustrates an embodiment where the emitters of the different measurement configurations are arranged to emit radiation at different wavelengths. Such a solution enables frequency multiplexing when combined with filtering measurement signals sensed by the photo sensor(s). In FIG. 10, each pattern of the emitters represents a distinct wavelength. Emitter(s) of a first measurement configuration may be configured to emit green light, while emitter(s) of a second measurement configuration may be configured to emit infrared light. The emitter(s) of the third measurement configuration may emit light at yet another wavelength. The green light has been discovered to be suitable for measuring heart activity during the physical exercise where motion artefacts may be present. Infrared light may be optimal for measuring the oxygen saturation. With respect to the sensor part, the photo sensor may be coupled to a plurality of parallel signal lines, wherein a filter is provided on each signal line. Each filter may be configured to provide a pass band on one of the frequency bands of the radiation emitted by the emitters. Accordingly, the radiation emitted by the different emitters may be separated in the photo sensor part, and each resulting signal may be processed by using a distinct signal processing algorithm associated with each wavelength measurement. In the embodiment of FIG. 10, the emitters of the different measurement configurations may emit simultaneously or with different emission timings. Since the signals sensed by the photo sensor from different emitters can be separated based on their wavelengths, the emission timings may be irrelevant.

Figure 11:
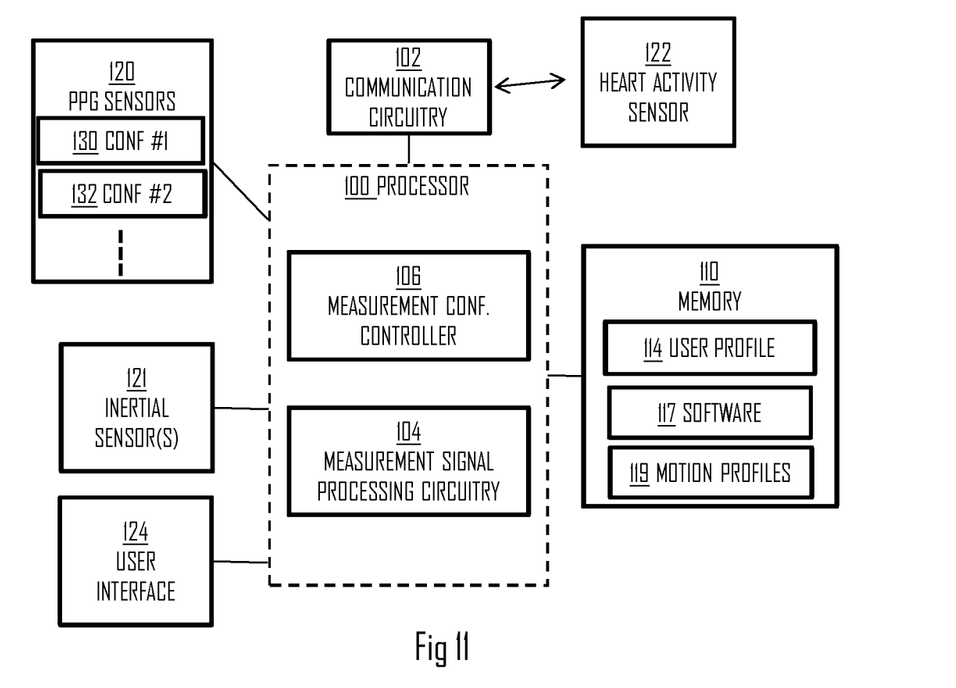
FIG. 11 illustrates a block diagram of an apparatus according to an embodiment of the invention.

FIG. 11 illustrates an embodiment of a block diagram of the apparatus, e.g. the wrist device 12 or the ear device 14. The apparatus may comprise an electronic device comprising at least one processor 100 and at least one memory 110. The processor 100 may form or be a part of a processing circuitry. The apparatus may further comprise a user interface 124 comprising a display screen or another display unit, an input device such as one or more buttons and/or a touch-sensitive surface, and an audio output device such as a loud-speaker. In some embodiments, the user interface 124 comprises a haptic output device configured to provide haptic indications to the user 20.

The processor 100 may comprise a measurement signal processing circuitry 104 configured to process measurement signals acquired from the photo sensor(s) of the measurement configurations. In some embodiments, the measurement signal processing circuitry is configured to acquire the measurement signals via different measurement channels and to combine signals of the measurement channels according of a determined logic, as described below.

The apparatus may comprise a communication circuitry 102 connected to the processor 100. The communication circuitry may comprise hardware and software suitable for supporting Bluetooth® communication protocol such as Bluetooth Smart specifications. It should be appreciated that other communication protocols are equivalent solutions as long as they are suitable for establishing a personal area network (PAN) or suitable for measurement scenarios described in this document. The processor 100 may use the communication circuitry 102 to transmit and receive frames according to the supported wireless communication protocol. The frames may carry a payload data comprising the above-described measurement data such as PPG measurement data. In some embodiments, the processor 100 may use the communication circuitry 109 to transmit the measurement data to another apparatus, e.g. to a cloud server storing the user's 20 user account.

In an embodiment, the apparatus comprises at least one heart activity sensor in the form of a PPG sensor. The PPG sensor may comprise one or more PPG sensor heads described above. The PPG sensor may comprise a plurality of measurement configurations 130, 132, . . . as described above. Additionally, the apparatus may communicate with at least one heart activity sensor 122 through the communication circuitry 102. The at least one heart activity sensor 122 may comprise an external heart activity sensor with respect to the apparatus, e.g. a heart activity sensor configured to measure electrocardiogram (ECG) of the user 20. The heart activity sensor(s) 122 may comprise different or different type(s) heart activity sensor(s) than the sensor(s) 120.

The apparatus may further comprise one or more inertial sensors 121. An inertial sensor may be a gyroscope or an accelerometer, and the apparatus may comprise the gyroscope and/or one or more accelerometers, e.g. a tri-axial accelerometer. The inertial sensor may be used to measure motion of the apparatus, and the measured motion may be used to reduce the above-mentioned motion interference or motion artefacts in a PPG measurement signal.

The processor 100 may further comprise a measurement configuration controller 106 configured to select measurement configurations 130, 132, . . . from the available sets of optical emitters and one or more photo sensors and/or control the operation of the multiple measurement configurations. The controller 106 may, for example, control the time-multiplexing of the measurement configurations, as described above. Additionally, the controller 106 may selectively switch measurement configurations on and off. The measurement configurations 130, 132, . . . may be fixed such that the measurement configuration controller 106 only switches the measurement configurations 130, 132, . . . on and off, or the measurement configuration controller 106 may create new measurement configurations from the available set of emitters and photo sensors dynamically according to a determined criterion.

The memory 110 may comprise one or more computer program products (software 117) configuring the operation of the processor 100 and its circuitries 104, 106. The memory 110 may further store a user profile 114 of the user 20. The user profile may store information on the user 20 and the user's personal characteristics such as age, gender, weight, height, performance indices, heart rate zones, speed zones, and similar parameters commonly used in connection with training computers. The memory 110 may further store one or more sport profiles 119 (e.g. running, cycling, swimming, skiing, tennis, badminton, strength training, mobility training, indoor sports, and outdoor sports). In connection with each sport profile, the associated measurement configurations of the PPG sensor may be defined. This may be understood such that a subset of all the measurement configurations described above in connection with any embodiment may be associated with a sport profile, and different sport profiles may be associated with different measurement configurations. This enables the controller 106 to selectively switch the measurement configurations according to the selected sport profile, as described below with reference to FIG. 12.

Figure 12:
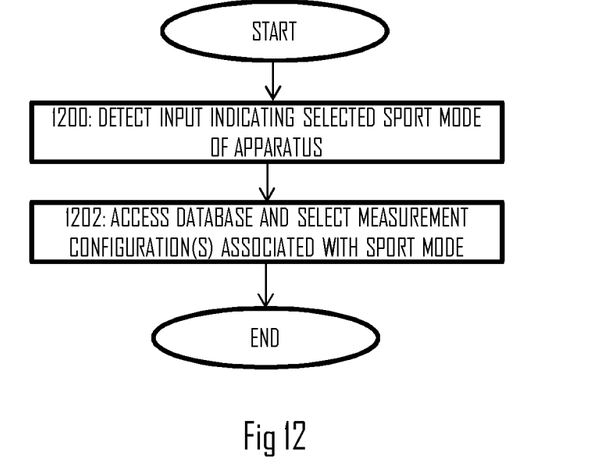
FIG. 12 illustrates an embodiment for selecting measurement configurations on the basis of a sport profile.

Referring to FIG. 12, the apparatus may provide use different measurement configurations for different motion profiles. The motion profiles 119 stored in the memory 110 may define unique measurement configurations of the PPG sensors. For example, the different motion profiles may employ different numbers of emitters and/or photo sensors. A motion profile associated with rapid motions may employ a higher number of emitters and/or photo sensors than a sport profile associated with slow motion. For example, badminton or tennis as a sport motion profile may employ a higher number of emitters and/or photo sensors than long distance running. Each motion profile stored in the memory 110 may be associated with a measurement mode of the apparatus. The measurement mode may define one or more measurement configurations used for acquiring measurement data when the motion profile is selected. In block 1200, the processor 100 detects an input indicating selection of a motion profile, e.g. a sport profile. The input may be a user input received through the user interface 124 from the user 20 selecting the sport profile, e.g. before starting a physical exercise. The input may be another input, e.g. a motion detection input indicating that the user has turned in and is sleeping, wherein the input may indicate a sleep motion profile. Another motion detection input may indicate intensive motion profile, e.g. when the user is moving rapidly in a situation where the user has not selected any sport profile in the apparatus. The situation may be such that the apparatus monitors daily activity of the user, and the user is performing rapid motions during normal activities. Upon receiving the input, the processor may access the database storing the motion profiles 119 and retrieve a measurement configuration or configurations associated with the indicated motion profile. In an embodiment, the processor 100 may activate the retrieved measurement configuration(s) immediately upon retrieval, e.g. without any further input. This may be applicable in the sleep motion profile, for example, wherein the processor 100 activates an infrared optical emitter or emitters and associated photo sensor(s) upon detecting the sleep motion profile. In another embodiment, upon receiving another input triggering a start of a measurement mode of the apparatus, the measurement configuration controller 106 may activate the measurement configuration(s) 130, 132 . . . associated with the selected sport profile as a response to the other input.

During the measurement mode, the measurement configuration controller 106 may selectively activate and/or deactivate one or more measurement configurations. For example, the measurement signal processing circuitry 104 may estimate the quality of the measurement signals received through the measurement channels and, upon detecting signal quality below a determined threshold, output a notification to the measurement configuration controller 106. Upon receiving the notification, the measurement configuration controller 106 may take additional measurement configuration 130, 132 . . . into use, thus providing an extra measurement channel.

Figure 13:
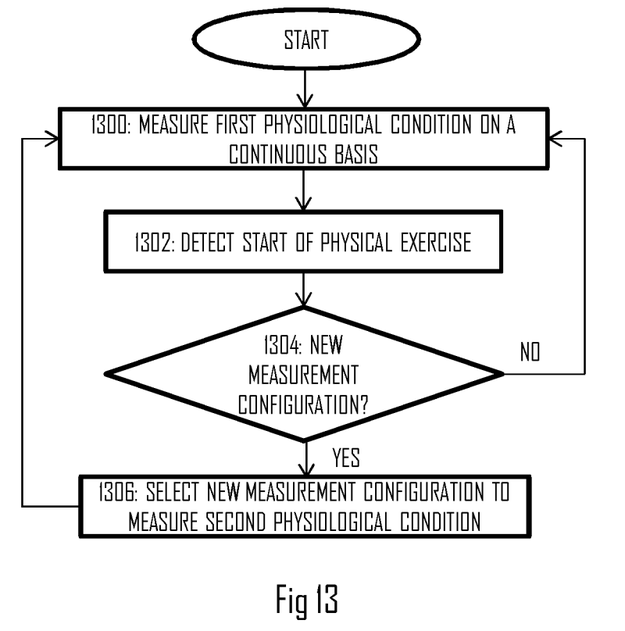
FIG. 13 illustrates a flow diagram of a process for concurrent utilization of multiple measurement configurations according to an embodiment of the invention.

FIG. 13 illustrates a flow diagram illustrating the use of multiple measurement configurations concurrently from another perspective. The PPG sensor may provide multiple measurement configurations, wherein at least some of the measurement configurations are dedicated for a certain purpose. For example, an emitter radiating at a determined wavelength may be better suited for measuring one physiological condition than another. Infrared light may be suitable for measuring the oxygen saturation while the green light is suitable for measuring the heart rate during the physical exercise. These different physiological conditions may be measured in a different manner, time-wise. For example, a certain measurement configuration may measure a first physiological condition on a continuous basis. Therefore, the measurement configuration controller 106 may configure the measurement configuration to carry out measurements on the continuous basis in block 1300. The continuous basis may be defined such that the measurements are carried out at least whenever the apparatus is attached to the user 20. The attachment may be detected by using a motion sensor. If the motion sensor detects motion, it may be detected that the user is wearing the apparatus and the measurement configuration controller 106 may carry out block 1300. Another sensor may be equally used, e.g. a pressure sensor or a proximity sensor detecting that the apparatus is in a contact with the user's skin, wrist, arm, or ear.

In block 1302, the apparatus detects a start of a physical exercise. The detection may be based on the user triggering the above-described measurement mode in the apparatus or the user indicating the selected sport profile. As a consequence, the measurement configuration controller 106 may determine whether or not the detection causes a need to activate a new measurement configuration (block 1304). If the new measurement configuration is needed, the measurement configuration controller 106 may select and activate a new measurement configuration in the PPG sensor to measure a second physiological condition, e.g. the heart rate (block 1306). When, the apparatus detects an end of the measurement mode or the physical exercise, the measurement configuration controller may deactivate the measurement configuration activated in block 1306. Accordingly, the measurement configuration may be used for a limited time period of the total time when the device is attached to the user 20. The at least two measurement configurations measuring the different physiological conditions may be in parallel use.

In an embodiment, the measurement configuration controller 106 may activate and deactivate a measurement configuration by using time as a reference. For example, if the apparatus is configured to monitor quality of sleep by using the PPG sensor, the measurement configuration controller may activate one or more measurement configurations dedicated for this purpose when detecting bedtime of the user. The detection may be based on a clock or based on detecting motion of the user. Motion sensors may be used to detect when the user is sleeping from a position and/or motion of the user, and the measurement configuration controller 106 may employ outputs of the motion sensor to activate and deactivate the measurement configuration(s) measuring the quality of sleep.

Figure 14:
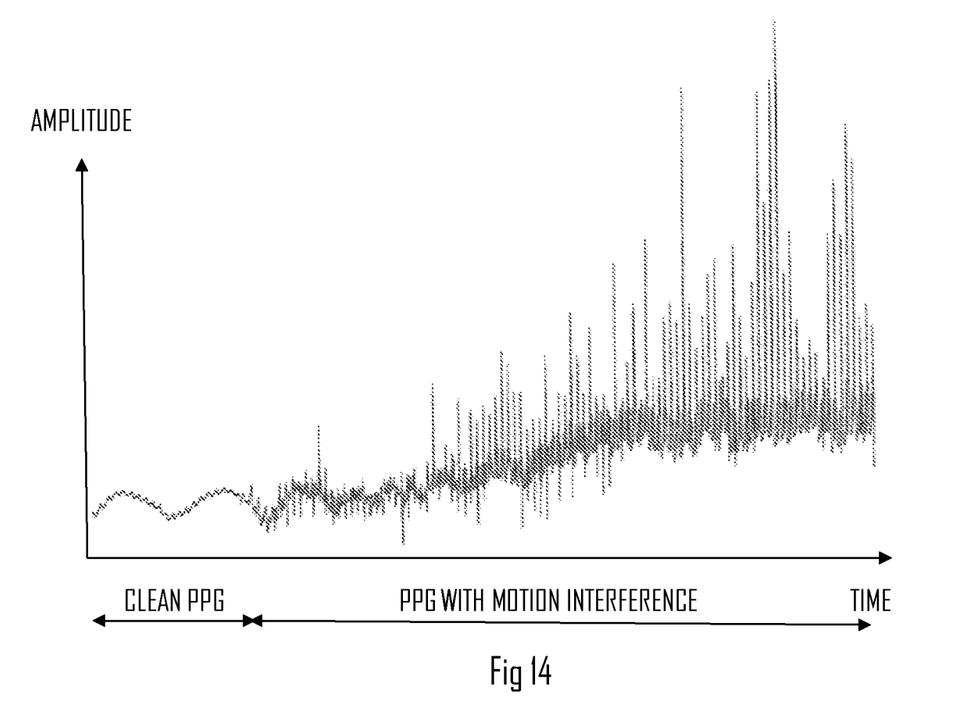
FIG. 14 illustrates the effect of motion interference on PPG measurements.

In an embodiment, the measurement signal processing circuitry 104 is configured to evaluate the signal quality of at least one measurement signal acquired from at least one measurement channel. As described above, the PPG measurement signal may by susceptible to motion interference. The motion interference may be caused by loose attachment of the apparatus to the user's 20 skin. FIG. 14 illustrates an effect of the motion interference on a clean PPG signal. As can be seen, the motion interference degrades the quality of the measurement signal and makes the detection of certain signal patterns in the PPG signal more difficult.

Figure 15:
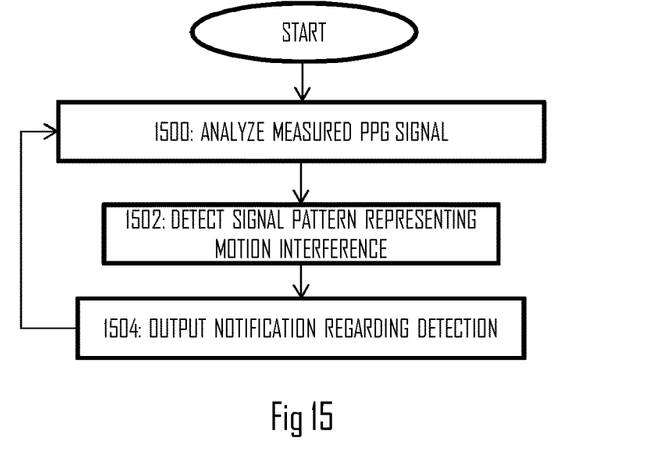
FIG. 15 illustrates a flow diagram of a process for detecting the motion interference according to an embodiment of the invention.

FIG. 15 illustrates an embodiment for analysing the measurement signals in the apparatus. Referring to FIG. 15, the measurement signal processing circuitry 104 may process a PPG measurement signal acquired from at least one measurement configuration (block 1500), to detect a signal pattern representing motion interference in the measurement signal (block 1502), and to output a notification regarding the detection (block 1504). In an embodiment, the measurement signal processing circuitry 104 is configured to estimate variance of the measurement signal and, upon detecting that the variance exceeds a threshold, output the notification. As seen in FIG. 14, the variance of the interfered PPG signal is higher than the variance of the clean PPG signal. Another solution could be comparing an amplitude of the PPG measurement signal with an amplitude threshold, and upon detecting that the amplitude exceeds the amplitude threshold, outputting the notification. In yet another embodiment, the measurement signal processing circuitry may compute a Fourier transform of the PPF measurement signal and compare samples of the transformed PPG measurement signal with a threshold. If one or more samples exceed the threshold, the apparatus may output the notification.

In an embodiment, the notification in block 1504 is output to the user interface 124 and informs the user 20 to check contact between the PPG sensor apparatus and the user's skin 20. The output may indicate the user 20 to attach the apparatus more tightly to the user's skin.

In an embodiment, the measurement signal processing circuitry 104 may use the multiple measurement channels to compute a metric representing a physiological condition such as the heart rate, oxygen saturation, and/or energy expenditure. The use of the multiple measurement channels in the computation of the metric may improve the performance of the computation and result in a more reliable metric than when using a single measurement channel.

Figure 16:
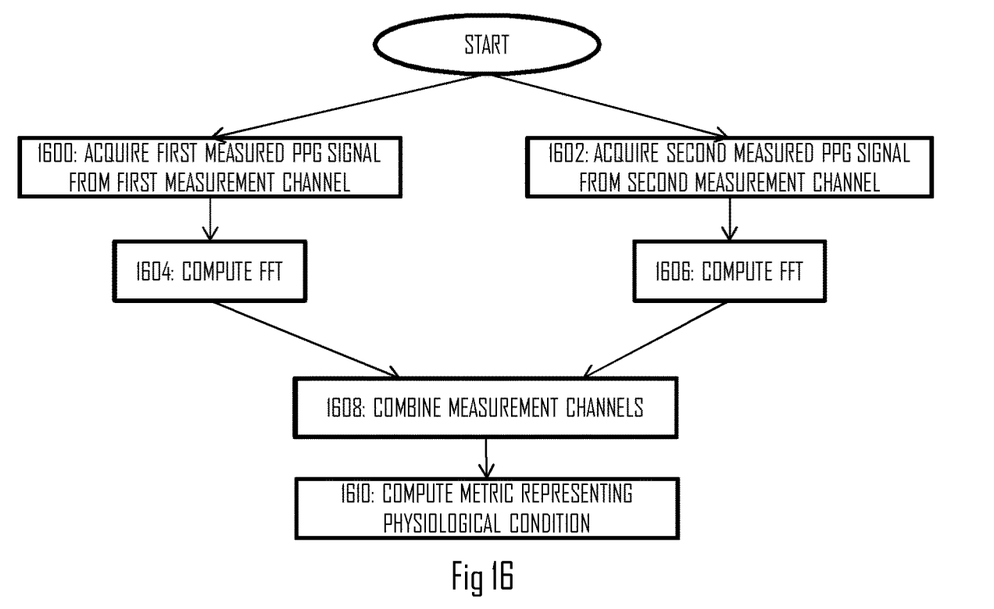
FIG. 16 illustrates a flow diagram of a process for combining measurement channels according to an embodiment of the invention.

In an embodiment, the measurement signal processing circuitry 104 may combine signals associated with the different measurement channels at a point in the processing. FIG. 16 illustrates an embodiment for carrying out the combining. Referring to FIG. 16, the measurement signal processing circuitry 104 acquires a first PPG measurement signal from a first measurement channel associated with a first measurement configuration (block 1600) and, further, acquires a second PPG measurement signal from a second measurement channel associated with a second measurement configuration (block 1602). The measurement configurations may be any two measurement configurations described above in connection with any one of FIGS. 3 to 6, for example. In block 1604, the measurement signal processing circuitry computes a (fast) Fourier transform of the first measurement signal. In block 1606, the measurement signal processing circuitry computes a (fast) Fourier transform (FFT) of the second measurement signal. In block 1608, the measurement signal processing circuitry combines the Fourier-transformed first and second measurement signals, e.g. by carrying out a sample-vise summing operation. Another combining method may be carried out. For example, the measurement signal processing circuitry may weigh the signals with different weighting factors before the summing, or it may carry out selection combining in which case it selects one of the measurement signals. After the combining, the measurement signal processing circuitry may estimate the metric representing the physiological condition.

The combining may be used to reduce the motion interference. When the measurement signals are measured by different measurement configurations and the measurement channels are substantially orthogonal or uncorrelated, the motion interference can be considered as uncorrelated noise while the PPG signal is correlated in the measurement signals. The combining of the two signals by summing them together may then attenuate the motion interference while amplifying the PPG signal components, thus improving signal quality and the quality of estimation of the metric.

In another embodiment, the measurement signal processing circuitry 104 reduces the motion interference by employing motion measurement signals received from the inertial sensor(s) 121. In an embodiment, the apparatus computes an FFT of the PPG measurement signal(s) acquired by using one or more of the above-described measurement configurations and, further, computes an FFT of a motion measurement signal received from the inertial sensor(s) 121. The measurement signal processing circuitry may determine one or more frequency components containing a high amount of motion interference from the FFT of the motion measurement signal and eliminate these frequency components from the FFT of the PPG measurement signal. In this manner, periodic motion interference may be excised from the PPF measurement signal.

In another embodiment, the measurement signal processing circuitry may employ the motion measurement signal as supplement for determining a physiological condition under a circumstance where estimation of the physiological condition from the PPG measurement signal is not temporarily possible, e.g. high interference or poor attachment of the apparatus to the user's skin. The apparatus may provide a mapping database mapping a feature of the motion measurement signal to the physiological condition. In an embodiment, the feature is periodicity of the motion measurement signal, and the physiological condition is the heart rate. The heart rate is a function of a degree of motion. A further input may be a sport profile of a physical exercise selected by the user, and the apparatus may have selected one or more measurement configurations associated with the sport profile, as described above. Under normal conditions, the apparatus may measure the physiological condition such as the heart rate or energy expenditure from the PPG measurement signal(s) acquired by using one or more measurement channels associated with the one or more measurement configurations. Upon detecting that the estimation of the physiological condition from the PPG measurement signal(s) is not possible, the measurement signal processing circuitry 104 may activate a motion estimation algorithm that estimates the physiological condition from the motion measurement signal(s). In an embodiment, the motion estimation algorithm takes the latest value of the physiological condition estimated from the PPF measurement signal(s), monitors a change in the feature of the motion measurement signal, and adjusts the latest value of the physiological condition on the basis of the change. For example, if the physiological condition is the heart rate and the feature is the periodicity of the motion, if the periodicity decreases, the motion estimation algorithm may decrease the value representing the physiological condition. If the periodicity increases, the motion estimation algorithm may increase the value representing the physiological condition. In another embodiment, the motion estimation algorithm may map an absolute value of the feature to the value of the physiological condition by using the mapping database.

In the embodiment of FIG. 16, the combining is carried out for a transformed measurement signal. The combining may be carried out at a different stage in other embodiments. For example, the measurement signal processing circuitry 104 may compute the metric independently for each measurement channel and then combine the metrics representing the different measurement channels. In other embodiments, time-domain representations of the measurement signals may be combined.

Figure 17:
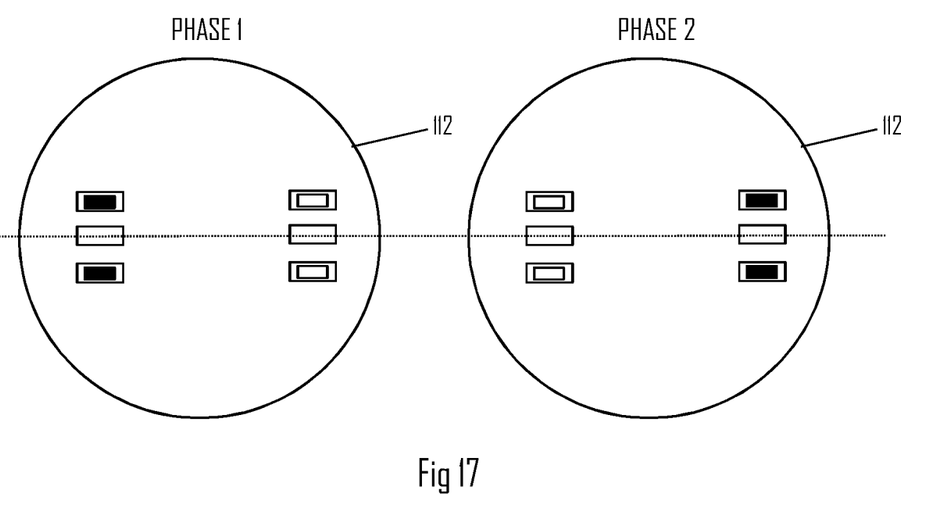
FIG. 17 illustrates another embodiment employing the measurement configuration of FIG. 8.

FIG. 17 illustrates another embodiment employing the same sensor arrangement as the embodiment of FIG. 8 but the illumination of the optical emitters is configured in a different manner. In the embodiment of FIG. 17, there exist two mutually orthogonal measurement configurations: a first measurement configuration on one half of the device 112 comprising multiple optical emitters and a photo sensor; and a second measurement configuration on the opposite half of the device 112 comprising a plurality of optical emitters and a photo sensor. In each measurement configuration, multiple optical emitters are associated with a photo sensor. In this embodiment, multiple optical emitters of the same measurement configuration are configured to emit simultaneously while optical emitters of the other measurement configuration(s) are not emitting. Referring to FIG. 17, the emitters of the first measurement configuration are emitting in a first phase, and the emitters of the second measurement configuration are emitting in a second phase following the first phase. In this manner, each measurement configuration may be configured to emit at a time and in an ordered manner. When all the phases have been completed and all the measurement configurations have illuminated their emitters, the procedure may start again from the first phase.

The embodiment of FIG. 17 is applicable to the other measurement configurations described herein in a straightforward manner.

In an embodiment of FIG. 17, the measurement configuration controller 106 may control the order and activation of the phases. In other words, the measurement configuration controller 106 may determine which one of the measurement configurations shall emit at each time instant. The determination may be based on a phase of a physical exercise or type of measurements being carried out, for example. There may exist situations where measurements from a certain part of the skin is needed. The measurement configuration controller 106 may store information associated with the locations of the measurement configurations and thus be capable of carrying out the determination and carrying out the spatial focusing of the measurements.

In another embodiment of FIG. 17, even a higher number of phases may be obtained by arranging each optical emitter to emit at a time. For example, in a first phase, one of the emitters of the first measurement configuration is emitting; another one of the emitters of the first measurement configuration is emitting in a second phase; one of the emitters of the second measurement configuration is emitting in a third phase; and another one of the emitters of the second measurement configuration is emitting in a fourth phase. In this embodiment, each emitter is emitting at a time which enables a higher number of spatial measurement locations and measurement phases.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the processes described in connection with FIGS. 12 to 16 may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, and circuitry. In an embodiment, the at least one processor 100, the memory 110, and the computer program code form processing means or comprises one or more computer program code portions for carrying out one or more operations according to any one of the embodiments of FIGS. 12 to 16 or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 12 to 16 may be carried out by executing at least one portion of a computer program comprising corresponding instructions. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

It will be obvious to a person skilled in the art that, as the technology advances, the inventive concept can be implemented in various ways. The invention and its embodiments are not limited to the examples described above but may vary within the scope of the claims.

What is claimed is:

1. A wearable photoplethysmographic sensor apparatus wearable by a user, the wearable photoplethysmographic sensor comprising:
    a casing defining a surface;
    a plurality of optical emitters configured to emit radiation extending from the surface;
    at least one photo sensor configured to capture radiation emitted by at least a subset of the plurality of optical emitters, wherein at least a first measurement configuration and a second measurement configuration are defined by the plurality of optical emitters and the at least one photo sensor, wherein the first and the second measurement configurations provide different measurement channels by comprising at least partially different sets of at least one optical emitter and at least one photo sensor, the first and second measurement configurations defining different spatial configurations each of which is line symmetric with respect to an imaginary line along the surface, the plurality of optical emitters being disposed around the photo sensor;
    a memory storing at least one sport profile and, associated with the at least one sport profile, the first measurement configuration that shall be utilized when the sport profile is selected, the memory further storing an oxygen-saturation measurement profile for measuring oxygen saturation, the oxygen saturation measurement profile associated with the second measurement configuration that shall be utilized when the oxygen-saturation measurement profile is selected;
    a controller configured to receive an input indicating the sport profile to selectively activate the first measurement configuration on the basis of the received indication of the sport profile and further on the basis of the first measurement configuration associated with the sport profile in the memory, and to selectively activate, on the basis of selecting the oxygen-saturation measurement profile, the second measurement configuration to be in concurrent use with the first measurement configuration while using the same photo sensor; and
    a processing circuitry configured to compute concurrently a heart rate of the user by using the first measurement configuration and oxygen saturation of the user by using the second measurement configuration.

2. The photoplethysmographic sensor apparatus of claim 1, wherein the first measurement configuration comprises a first photo sensor and a plurality of optical emitters disposed symmetrically around the first photo sensor, and wherein the second measurement configuration comprises a second photo sensor different from the first photo sensor and a plurality of optical emitters disposed symmetrically around the second photo sensor.

3. The photoplethysmographic sensor apparatus of claim 1, wherein the first measurement configuration comprises a first photo sensor and a first set of optical emitters disposed symmetrically around the first photo sensor, and wherein the second measurement configuration comprises the first photo sensor and a second set of optical emitters disposed symmetrically around the second photo sensor, wherein the first set of optical emitters and the second set of optical emitters define different sets of optical emitters.

4. The photoplethysmographic sensor apparatus of claim 1, wherein the memory further stores a sleep motion profile associated with sleeping and, associated with the sleep motion profile, a third measurement configuration that shall be utilized when the sleep motion profile is selected, and wherein the processing circuitry is configured to receive an input indicating activation of the sleep motion profile, to selectively activate the third measurement configuration on the basis of the received indication of the sleep motion profile and further on the basis of the third measurement configuration being associated with the sleep motion profile in the memory.

5. The photoplethysmographic sensor apparatus of claim 1, wherein a third measurement configuration is defined by the plurality of optical emitters and the at least one photo sensor, wherein the controller is configured to enable the third measurement configuration at least always when the photoplethysmographic sensor apparatus is attached to the user.

6. The photoplethysmographic sensor apparatus of claim 1, wherein the sport profile associated with the first measurement configuration is a running profile, the memory further storing a tennis profile and, associated with the tennis profile, a third measurement configuration defined by the plurality of optical emitters and the photo sensor.

7. The photoplethysmographic sensor apparatus of claim 1, wherein the processing circuitry is configured to process a measurement signal acquired from at least one of the at least first and second measurement configuration to detect a signal pattern representing motion interference in the measurement signal, and to output a notification regarding the detection.

8. The photoplethysmographic sensor apparatus of claim 7, wherein the notification is output to a user interface and informs the user to check contact between the photoplethysmographic sensor apparatus and the user.

9. The photoplethysmographic sensor apparatus of claim 7, wherein the processing circuitry is configured to detect the signal pattern on the basis of variance of the measurement signal.

10. The photoplethysmographic sensor apparatus of claim 1, wherein the first and second measurement configurations are configured to perform measurements as multiplexed with respect to one another, wherein the multiplexing provides for the different measurement channels.

11. The photoplethysmographic sensor apparatus of claim 10, wherein the plurality of optical emitters of the second measurement configuration is configured to emit infrared light while at least one optical emitter of the first measurement configuration is configured to emit green light.

12. The photoplethysmographic sensor apparatus of claim 10, wherein emissions of at least one optical emitter of the first measurement configuration are time-multiplexed with emissions of at least one optical emitter of the second measurement configuration.

13. A wearable photoplethysmographic sensor apparatus wearable by a user, the wearable photoplethysmographic sensor comprising:
    a casing defining a surface;
    a plurality of optical emitters configured to emit radiation extending from the surface;
    at least one photo sensor configured to capture radiation emitted by at least a subset of the plurality of optical emitters, wherein at least a first measurement configuration and a second measurement configuration are defined by the plurality of optical emitters and the at least one photo sensor, wherein the first and the second measurement configurations provide different measurement channels by comprising at least partially different sets of at least one optical emitter and at least one photo sensor, the first and second measurement configurations defining different spatial configurations each of which is line symmetric with respect to an imaginary line along the surface;
a memory storing at least one sport profile and, associated with the at least one sport profile, the first measurement configuration that shall be utilized when the sport profile is selected, the memory further storing an oxygen-saturation measurement profile for measuring oxygen saturation, the oxygen saturation measurement profile associated with the second measurement configuration that shall be utilized when the oxygen-saturation measurement profile is selected;
a controller configured to receive an input indicating the sport profile to selectively activate the first measurement configuration on the basis of the received indication of the sport profile and further on the basis of the first measurement configuration associated with the sport profile in the memory, and to selectively activate, on the basis of selecting the oxygen-saturation measurement profile, the second measurement configuration to be in concurrent use with the first measurement configuration while using the same photo sensor; and
a processing circuitry configured to compute concurrently a heart rate of the user by using the first measurement configuration and oxygen saturation of the user by using the second measurement configuration, wherein the controller is configured to acquire a first set of measurement data from at least one photo sensor of the first measurement configuration and a second set of measurement data from at least one photo sensor of the second measurement configuration, and to combine the first set of measurement data and the second set of measurement data.

* * * * *